United States Patent [19]

Tritschler et al.

[11] Patent Number: 5,086,173
[45] Date of Patent: Feb. 4, 1992

[54] PROCESS FOR THE PREPARATION OF ALKYLHYDROXYANILINOTHIOTRIAZINE DERIVATIVES

[75] Inventors: Wolfgang Tritschler, Binzen, Fed. Rep. of Germany; Heinz Steiner, Münchenstein, Switzerland; Helmut Prestel, Bruchsal; Rudolf Maul, Lorsch/Hessen, both of Fed. Rep. of Germany

[73] Assignee: Ciba-Geigy Corporation, Ardsley, N.Y.

[21] Appl. No.: 699,067

[22] Filed: May 13, 1991

[30] Foreign Application Priority Data

May 18, 1990 [CH] Switzerland ............... 1701/90

[51] Int. Cl.$^5$ .................................. C07D 251/46
[52] U.S. Cl. ........................................ 544/211
[58] Field of Search ............................. 544/211

[56] References Cited

U.S. PATENT DOCUMENTS 3,156,690 11/1964 Dexter et al. .................. 544/211
3,240,749 3/1966 Dexter et al. .................. 544/211
3,255,191 6/1966 Dester et al. .................. 544/211
3,257,354 6/1966 Dexter et al. .................. 544/211

FOREIGN PATENT DOCUMENTS 0191983 8/1986 European Pat. Off. .
2122637 9/1972 France .
WO8910347 11/1989 PCT Int'l Appl. .

OTHER PUBLICATIONS

Albert J. Am. Chem. Soc. 76, 4985 (1954).
Gilman et al J. Org. Chem. 19, 1067 (1954).

*Primary Examiner*—John M. Ford
*Attorney, Agent, or Firm*—Harry Falber

[57] ABSTRACT

A process for the preparation of compounds of formula I

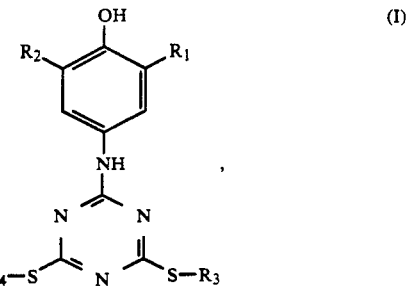

wherein $R_1$ and $R_2$ are each independently of the other hydrogen, $C_1$-$C_{12}$alkyl, $C_5$-$C_6$cycloalkyl or phenyl, and $R_3$ and $R_4$ are each independently of the other $C_1$-$C_{18}$alkyl, $C_5$-$C_6$cycloalkyl, phenyl, phenyl which is substituted by $C_1$-$C_6$alkyl and/or hydroxy, or phenyl-$C_1$-$C_4$alkyl. The process comprises reacting a compound of formula III

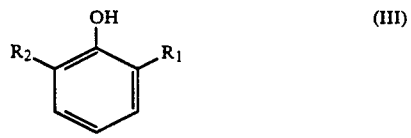

with a nitrite in aqueous or aqueous/organic medium to a compound of formula II

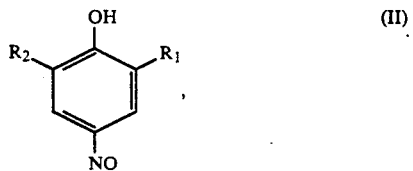

extracting said compound of formula II from the reaction solution with a solvent, hydrogenating said compound, without isolation, in the cited solvent and in the presence of a palladium catalyst, to the corresponding p-aminophenol, and reacting said aminophenol, without isolation, with cyanuric chloride and a compound of formula $HSR_3$ or $HSR_4$ or a mixture of compounds of formulae $HSR_3$ and $HSR_4$. The products are obtained in high yield and purity.

13 Claims, No Drawings

PROCESS FOR THE PREPARATION OF ALKYLHYDROXYANILINOTHIOTRIAZINE DERIVATIVES

The present invention relates to a process for the preparation of alkylhydroxyanilinothiotriazine derivatives in high yield without isolation of the intermediates obtained.

The alkylhydroxyanilinothiotriazine derivatives are obtained by nitrosation of the appropriate starting phenols to the alkylnitrosophenols and hydrogenation thereof to the aminophenols, and by subsequent condensation with cyanuric chloride and alkyl- or phenylmercaptans.

The preparation of alkylhydroxyanilinothiotriazine derivatives is disclosed in U.S. Pat. No. 3,156,690, U.S. Pat. No. 3,257,354, U.S. Pat. No. 3,255,191 and U.S. Pat. No. 3,240,749. In these references, all intermediates are isolated and the reduction of the nitrosophenol to the aniline is carried out with sodium hydrogensulfite. Aside from these processes, other processes are described in the literature for reducing substituted nitrosophenols to the corresponding aminophenols. Thus, for example, the possibility of reducing nitrosophenols with sodium hydrogensulfite or by zinc in acetic acid is described by E. Albert in J. Am. Chem. Soc. 76, 4985 (1954). Catalytic hydrogenations of nitrosophenols to aminophenols with Raney nickel are described by H. Gilman et al (J. Org. Chem. 19, 1067 (1954). A catalytic hydrogenation with Raney nickel is disclosed in FR-A-2 122 637 and the possibility of using other catalysts, such as palladium, platinum or cobalt, is mentioned. The preparation of dithiodialkanoamidophenols from the intermediates of the appropriate nitrosophenols and aminophenols is disclosed in EP-A-0 191 983. The hydrogenation step is carried out using palladium on carbon catalysts. A process for the preparation of N-acylated 3,5-dialkyl-4-aminophenols by hydrogenation of the appropriate nitrosophenols and N-acylation of the resultant aminophenols in the same solvent is disclosed in WO-A 89/1595.

The alkylhydroxyanilinothiotriazine derivatives, in particular 6-(3',5'-dialkyl-4'-hydroxyphenylamino)-2,4-dialkylthio-1,3,5-triazines, are useful substances, some of which are commercially available, for stabilising materials which are sensitive to oxidative, thermal and/or light-induced degradation. It is therefore of interest to prepare these compounds successfully on an industrial scale and in an ecologically safe manner.

It has now been found that the process can be carried out with particular advantage without isolating the intermediates and by carrying out the reduction step with hydrogen in the presence of a palladium catalyst.

Specifically, the invention relates to a process for the preparation of alkylhydroxyanilinothiotriazine derivatives of formula I

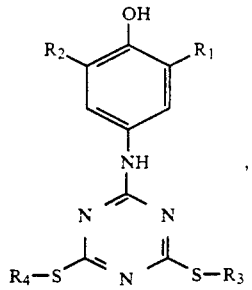

wherein $R_1$ and $R_2$ are each independently of the other hydrogen, $C_1$–$C_{12}$alkyl, $C_5$–$C_6$cycloalkyl or phenyl, and $R_3$ and $R_4$ are each independently of the other $C_1$–$C_{18}$alkyl, $C_5$–$C_6$cycloalkyl, phenyl, phenyl which is substituted by $C_1$–$C_6$ alkyl and/or hydroxy, or phenyl-$C_1$–$C_4$alkyl, which process comprises reacting a compound of formula III

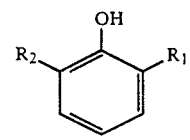

with a nitrite in aqueous or aqueous/organic medium to a compound of formula II

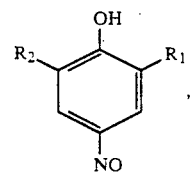

extracting said compound of formula II from the reaction solution with a solvent, catalytically hydrogenating said compound, without isolation, in the cited solvent and in the presence of a palladium catalyst, to the corresponding p-aminophenol, and reacting said aminophenol, without isolation, with cyanuric chloride and a compound of formula $HSR_3$ or $HSR_4$ or a mixture of compounds of formulae $HSR_3$ and $HSR_4$.

$R_1$ and $R_2$ as $C_1$–$C_{12}$alkyl may be linear or branched and are typically methyl, ethyl, n-propyl, isopropyl, n-butyl, isobutyl, tert-butyl, n-pentyl, isopentyl, tert-pentyl, hexyl, heptyl, n-octyl, isooctyl, nonyl, decyl, undecyl or dodecyl. The preferred meaning is tert-butyl.

$R_1$ and $R_2$ as $C_5$–$C_6$cycloalkyl are cyclopentyl or cyclohexyl.

$R_1$ and $R_2$ are preferably hydrogen or $C_1$–$C_{12}$alkyl, most preferably $C_1$–$C_4$alkyl.

In another preferred embodiment of the invention, $R_1$ and $R_2$ are identical. Most preferably, $R_1$ and $R_2$ are identical and are tert-butyl.

$R_3$ and $R_4$ as $C_1$–$C_{18}$alkyl may be linear or branched and have the meanings given for $R_1$ and $R_2$, and are additionally typically tridecyl, tetradecyl, pentadecyl, hexadecyl, heptadecyl or octadecyl, preferably $C_1$–$C_{12}$alkyl, most preferably n-octyl.

$R_3$ and $R_4$ as $C_5$–$C_6$cycloalkyl have the same meanings as given for $R_1$ and $R_2$.

$R_3$ and $R_4$ as phenyl which is substituted by one or more $C_1$-$C_6$alkyl groups may be phenyl which is substituted by 1 to 3, preferably 1 or 2, alkyl groups, preferably methyl groups. Typical examples of such groups are tolyl, xylyl or mesityl. $R_3$ and $R_4$ as $C_1$-$C_6$alkyl-substituted phenyl may also typically be ethylphenyl, diethylphenyl, propylphenyl, dipropylphenyl, butylphenyl, ethylmethylphenyl, methylpropylphenyl, butylmethylphenyl or ethylpropylphenyl.

$R_3$ and $R_4$ as phenyl which is substituted by one or more hydroxy and/or $C_1$-$C_6$alkyl groups may suitably be hydroxyphenyl, dihydroxyphenyl, resorcyl, cresyl, ethylhydroxyphenyl, propylhydroxyphenyl, butylhydroxyphenyl, pentylhydroxyphenyl, hexylhydroxyphenyl, dimethylhydroxyphenyl, diethylhydroxyphenyl, dipropylhydroxyphenyl, ethylmethylhydroxyphenyl, methylpropylhydroxyphenyl, butylmethylhydroxyphenyl, methylpentylhydroxyphenyl, ethylpropylhydroxyphenyl or butylethylhydroxyphenyl.

$R_3$ and $R_4$ as phenyl-$C_1$-$C_4$alkyl may be benzyl, phenylethyl, α-methylbenzyl, phenylpropyl, α,α-dimethylbenzyl, phenyl(methylpropyl) or phenylethyl, preferably benzyl. Preferably $R_3$ and $R_4$ are $C_1$-$C_{12}$alkyl.

In a preferred process, $R_1$ and $R_2$ are each independently of the other hydrogen or $C_1$-$C_{12}$alkyl, and $R_3$ and $R_4$ are each independently of the other $C_1$-$C_{12}$alkyl.

In a further preferred embodiment of the invention $R_3$ and $R_4$ are identical.

Suitable nitrites for carrying out the nitrosation are typically alkali metal nitrites or alkaline earth metal nitrites, such as $NaNO_2$, $KNO_2$, $Ba(NO_2)_2$ or $Ca(NO_2)_2$. Alkali metal nitrites are preferred, and sodium nitrite is especially preferred.

It is preferred to carry out the process of this invention in a solvent which is inert under the conditions of the hydrogenation step.

Illustrative examples of suitable solvents are ketones, aromatic, cycloaliphatic or aliphatic hydrocarbons, ethers or esters, mixtures of such solvents as well as mixtures thereof with water. Particularly preferred ketones are aliphatic and cycloaliphatic ketones.

Aliphatic ketones are typically acetone, diethyl ketone, methyl ethyl ketone, methyl isobutyl ketone or hexanone. Methyl ethyl ketone and methyl isobutyl ketone are preferred. A cycloaliphatic ketone is typically cyclohexanone. Suitable aromatic hydrocarbons are benzene, toluene or xylene.

Typical examples of suitable ethers are diethyl ether or tert-butylmethyl ether. A suitable ester is typically ethyl acetate. Aliphatic or cycloaliphatic hydrocarbons are typically hexane, heptane or cyclohexane.

Particularly preferred solvents are ketones. Surprisingly, ketones are completely inert under the hydrogenation conditions, i.e. neither a hydrogenation of the ketone nor a reductive alkylation of the aminophenol derivative with the ketone is observed.

In a particularly preferred process, methyl isobutyl ketone, methyl ethyl ketone, or a mixture thereof with water is used as solvent.

The catalytic hydrogenation of the process is conveniently carried out in the temperature range from 20° to 100° C., preferably from 20° to 80° C., most preferably from 30° to 70° C. The hydrogen pressures at which the catalytic hydrogenation is carried out are not critical and can vary over a wide range, but are conveniently 1-200 bar, preferably 1-100 bar, most preferably 1-50 bar.

At which hydrogen pressure the process is carried out will also depend on the type of hydrogenation reactor used.

The hydrogenation time can vary over a wide range and depends on the catalyst used, on the hydrogen pressure, on the reaction temperature and on the reactor used. It can be typically from 1 minute to 2 hours, preferably from 5 minutes to 1 hour, for example from 10 to 30 minutes. Naturally the reaction time will be shortened by raising the hydrogen pressure and/or the temperature.

In a preferred process, the amount of catalyst used will be 0.01-5.0% by weight, preferably 0.02-2% by weight, most particularly 0.1-2.0% by weight, typically 0.2-1.5% by weight, most preferably 0.2-1% by weight, based on the compound of formula II.

In the process of the invention, the catalytic hydrogenation is carried out in the presence of a palladium catalyst. This catalyst will conveniently be in a form conventionally used for this purpose, i.e. the respective metal is applied to a carrier, typically to activated carbon, diatomaceous earth, alumina, barium sulfate and the like. The catalyst can be activated by an additional metal, for example by magnesium, zirconium or molybdenum. In the process of this invention it is preferred to use a palladium catalyst on a carrier, especially a palladium on carbon (Pd/C) catalyst.

The amount of catalyst on the carrier (charge) is conveniently 0.5-10%, preferably 0.5-5.0%, most preferably 0.5-2.0%.

The process of the invention is conveniently carried out such that first the phenol of formula III is reacted with the nitrosating reagent (preferably $NaNO_2$), in aqueous or aqueous/organic reaction medium, preferably in the presence of an acid. This is done by adding the phenol to the solvent or solvent mixture and then adding a solution of the nitrosating reagent in water dropwise. After a portion of the solvent has been distilled from the reaction mixture (for example, if an aqueous/organic solvent mixture is used, then the organic solvent is removed as an azeotrope with water), the resultant p-nitroso intermediate of formula II is extracted from the residual aqueous reaction mixture with a solvent which is inert under the chosen hydrogenation conditions. The extracted solvent phase can then be transferred, preferably under inert conditions, to an autoclave which contains the catalyst. By pressurising with hydrogen, raising the temperature and stirring, the p-nitroso compound of formula II is hydrogenated to the corresponding. p-aminophenol. When the reaction is complete, the catalyst is removed by filtration and the filtrate is reacted with an alkyl- or phenylmercaptan of formula $HSR_3$ and/or $HSR_4$ and cyanuric chloride. This reaction is conveniently carried out under customary conditions by charging the cyanuric chloride to the same solvent in which the nitroso compound was extracted and hydrogenated, and the filtrate containing the p-aminophenol, as well as the alkyl- or phenylmercaptan, are added dropwise, with stirring and cooling. The reaction product is isolated by conventional methods such as distillation and/or crystallisation.

The hydrogenation step can be carried out in a batch process as well as in a semicontinuous process. In the semicontinuous process, the extraction solution is added continuously, after the nitrosation step, during the course of the hydrogenation against the hydrogen pressure to the hydrogenation reactor which contains the catalyst.

As stated above, the hydrogenation and the reaction with cyanuric chloride and the mercaptan can also be carried out in a mixture of the cited solvents with water. The reaction mixture contains a certain amount of water in any case from the extraction step. However, before the hydrogenation and/or before the last step additional water can be added. It is expedient to add water—if at all—in an amount such that, at the conclusion of the process, the solvent/water mixture can be distilled from the reaction mixture as an azeotrope.

It will be self-evident to the person skilled in the art that, in the last step, conveniently at least 2 mol of the compound $HSR_3$ and/or $HSR_4$ per mol of p-aminophenol and cyanuric chloride will be added according to the stoichiometric conditions. If it is desired to obtain compounds of formula I, wherein $R_3 \neq R_4$, then the reaction is preferably carried out with a mixture of two different mercaptans. However, $R_3 = R_4$ is preferred. In this case, ca. 2 molar equivalents of a mercaptan are added.

The reaction conditions in the nitrosation step and in the subsequent reaction with cyanuric chloride and mercaptan are not critical. Both reactions are carried out in a manner known per se as described in, for example, U.S. Pat. Nos. 3,156,690, 3,257,354, 3,255,191 and 3,240,749, provided the key features of the invention are observed.

It is preferred to carry out the nitrosation in the temperature range from $-20°$ to $+50°$ C., preferably from $-10°$ to $+30°$ C. As already mentioned, the reaction proceeds advantageously in aqueous/organic medium, in which case a water-miscible organic solvent may be used concurrently as organic solvent component, for example an alcohol such as a $C_1$–$C_5$alkanol, preferably methanol, ethanol, n-propanol, isopropanol, n-butanol, isobutanol and the like, or an aliphatic ketone, preferably acetone, diethyl ketone, methyl ethyl ketone or methyl isobutyl ketone, most preferably acetone. The nitrosation is normally carried out in the presence of an acid, typically a mineral acid such as sulfuric acid, phosphoric acid or, preferably, hydrochloric acid. The extraction of the nitroso compound of formula II can be performed direct from the reaction mixture; but sometimes it is expedient to distill off a portion of the reaction medium, for example to remove concurrently used solvent (such as the azeotropic distillation of an alcohol/water mixture). The residue is then extracted.

In the last step, the process is carried out in the temperature range from $-20°$ to $+70°$ C., preferably from $-10°$ to $+50°$ C., typically from $-10°$ to $+30°$ C. If the reaction mixture still contains no water, it is often expedient to add water, for example together with the cyanuric chloride. Upon completion of the reaction, the solvent can be readily removed by distillation as an azeotropic mixture with water. As HCl evolves during the reaction, it is especially expedient to add a base to the reaction mixture, for example a hydroxide of an alkali metal or alkaline earth metal, typically NaOH, KOH, $Ca(OH_2)$, $Mg(OH)_2$ and the like, or an organic amine, preferably a tri-$C_1$–$C_6$alkylamine (such as trimethylamine, triethylamine, tripropylamine or tributylamine). It is preferred to use an alkali metal hydroxide, in particular KOH, most preferably NaOH. Before the isolation of the product it is expedient to neutralise the base with an acid. In general, the addition of the cyanuric chloride, mercaptan and the base to the solution of the p-aminophenol can be made simultaneously or in any order. However, it is preferred to add first the mercaptan to the p-aminophenol, then to add this mixture (dissolved in an aqueous/organic or organic solvent) dropwise to the cyanuric chloride, and to add the base last.

Hitherto the reduction step in the preparation of alkylhydroxyanilinothiotriazine derivatives has been carried out with an inorganic reducing agent (such as sodium hydrogensulfite). This reduction has been environmentally undesirable, owing to the ensuing salt formation. In this regard, the catalytic hydrogenation provides an economic and environmentally more acceptable process. The decisive advantage of the process of this invention is that it is carried out without isolation of the intermediates, most particularly without isolation of the p-nitroso intermediate.

For carrying out the process of the invention, the chosen solvent should also have a sufficient solubility for all intermediates. At the same time, the chosen solvent must be inert under the given hydrogenation parameters and must not undergo change during the subsequent condensation. It should thus be a) able to extract the p-nitroso compound, b) inert under the reaction conditions of the hydrogenation, and c) a suitable reaction medium for the reaction of the hydrogenation product with alkyl- and phenylmercaptans and cyanuric chloride.

Surprisingly, owing to the aforementioned measures it is possible in the process of this invention to carry out the known process for the preparation of alkylhydroxyanilinothiotriazine erivatives, in which the intermediates were isolated, without isolating said intermediates and in high yield.

The invention is illustrated in more detail by the following Examples in which, and throughout the remainder of the the description and claims, parts and percentages are by weight, unless otherwise stated.

EXAMPLE 1

6-(4'-Hydroxy-3',5'-di-tert-butylanilino)-2,4-bis(n-octylthio)-1,3,5-triazine

In a 1 l glass reactor 44.4 g of 2,6-di-tert-butylphenol are suspended in a mixture of 125 g of isopropanol and 20 g of water. The suspension is cooled to 0° C., then 27.7 g of hydrochloric acid (32%) and 75 g of water are added and nitrosation is effected by the dropwise addition of 38.8 g of sodium nitrite solution (40%) at $-5°$ to $+20°$ C.

When the nitrosation is complete, 200 g of water are added and the isopropanol is distilled from the reaction mixture as an azetrope with water. Then 180 g of methyl ethyl ketone are added to extract the nitroso intermediate from the aqueous to the organic phase. At 60°–65° C. an orange-yellow upper phase and a clear, aqueous lower phase form. This lower phase is separated and discarded.

The upper phase is transferred under inert conditions (nitrogen blanketing) to a 300 ml autoclave containing 0.5 g of a 1% Pd on activated carbon catalyst. After pressurising with hydrogen at 10 bar, hydrogenation is carried out at 50° C. with efficient stirring. The conclusion of hydrogenation is clearly detected by the cessation of the hydrogen uptake after 2 molar equivalents with respect to the nitroso intermediate. The hydrogenation time is 0.3 hour.

The catalyst is removed by filtration and 62.3 g of octanethiol are added to the filtrate. This solution is added dropwise at $-5°$ to 0° C. over ca. 30 minutes to a mixture of 97 g of methyl ethyl ketone, 150 g of ice and 38.7 g of cyanuric chloride. After addition of 88.7 g of 30% sodium hydroxide solution the reaction mixture is heated to reflux for 1 hour and then the methyl ethyl ketone is removed by distillation as an azeotrope with water. The residual reaction mass is acidified with acetic acid, the aqueous lower phase is separated at 95°–97° C., further water is removed from the product melt by distillation, and 225 g of isopropanol are added. After cooling to 0° C. (onset of crystallisation at ca. 60° C.), the crystal are isolated by filtration, washed with 240 g of isopropanol and dried. Yield: 92% of theory.

Examples 2–7 are carried out in accordance with the general procedure of Example 1, but varying the parameters in the hydrogenation step. These parameters are indicated in Table 1.

TABLE 1

| Example | Pd on carbon in % | Amount of catalyst [g] | Temperature [°C.] | Pressure [bar] | Hydrogenation time [h] | Yield [%] |
|---|---|---|---|---|---|---|
| 2 | 1 | 0.5 | 40 | 10 | 0.7 | 92 |
| 3 | 1 | 0.5 | 50 | 5 | 0.6 | 92 |
| 4 | 1 | 0.5 | 50 | 40 | 0.2 | 92 |
| 5 | 3 | 0.5 | 50 | 10 | 0.3 | 89 |
| 6 | 1 | 0.2 | 50 | 10 | 1.0 | 92 |
| 7 | 1 | 1.0 | 50 | 10 | 0.2 | 92 |

Example 8

Example 1 is repeated, except that methyl isobutyl ketone is used in place of methyl ethyl ketone for the extraction of the nitroso intermedate from the aqueous to the organic phase. Methyl isobutyl ketone is therefore also used for the hydrogenation and subsequent working up of the reaction mass in place of methyl ethyl ketone. When working up the reaction mass (reflux and removal of the methyl isobutyl ketone by distillation before crystallisation of the product), the temperature is adjusted in accordance with the boiling range of the different solvent. The yield is 91% of theory.

Example 9

Example 1 is repeated, except that a semicontinuous process is carried out instead of a batch process. The procedure is that, after the extraction of the nitroso intermediate from the aqueous to the organic phase, the resultant solution is not transferred at once to the hydrogenation reactor, but is fed continuously in the course of the hydrogenation, against the hydrogen pressure, to the reactor, which contains all the catalyst and methyl ethyl ketone in an amount sufficient to disperse the catalyst, whereupon the reduction of the nitroso intermediate to the amine intermediate takes place. Upon cessation of the hydrogen uptake, the further steps described in Example 1 are carried out. The product is isolated in a yield of 89% of theory.

What is claimed is:

1. A process for the preparation of an alkylhydroxyanilinothiotriazine derivative of formula I

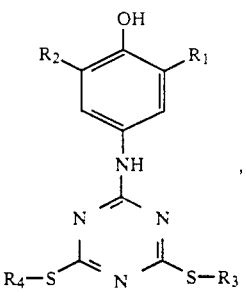

wherein $R_1$ and $R_2$ are each independently of the other hydrogen, $C_1$–$C_{12}$alkyl, $C_5$–$C_6$cycloalkyl or phenyl, and $R_3$ and $R_4$ are each independently of the other $C_1$–$C_{18}$alkyl, $C_5$–$C_6$cycloalkyl, phenyl, phenyl which is substituted by $C_1$–$C_6$ alkyl and/or hydroxy, or phenyl-$C_1$–$C_4$alkyl, which process comprises reacting a compound of formula III

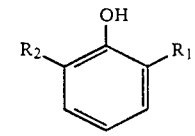

with a nitrite, in aqueous or aqueous/organic medium, to a compound of formula II

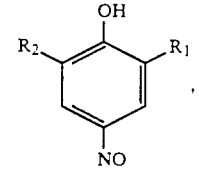

extracting said compound of formula II from the reaction solution with a solvent, hydrogenating said compound, without isolation, in the cited solvent and in the presence of a palladium catalyst, to the corresponding p-aminophenol, and reacting said aminophenol, without isolation, with cyanuric chloride and a compound of formula $HSR_3$ or $HSR_4$ or a mixture of compounds of formulae $HSR_3$ and $HSR_4$.

2. The process of claim 1, wherein the process is carried out in a solvent which is inert under the reaction conditions.

3. The process of claim 1, wherein the solvent is a ketone, an ester, an ether, an aromatic, aliphatic or cycloaliphatic hydrocarbon, or a mixture of such solvents or a mixture of at least one of said solvents with water.

4. The process of claim 3, wherein the solvent is methyl isobutyl ketone, methyl ethyl ketone or a mixture of said solvents with water.

5. The process of claim 3, wherein the catalytic hydrogenation is carried out in the temperature range from 20° to 100° C.

6. The process of claim 1, wherein the catalytic hydrogenation is carried out in the pressure range from 1 to 200 bar.

7. The process of claim 1, wherein the amount of catalyst is 0.01 to 5.0% by weight, based on the compound of formula II.

8. The process of claim 1, wherein the hydrogenation catalyst is Pd on a carrier.

9. The process of claim 8, wherein the amount of Pd on the carrier is 0.5–5%.

10. The process of claim 1, wherein $R_1$ and $R_2$ are each independently of the other hydrogen or $C_1$–$C_{12}$alkyl, and $R_3$ and $R_4$ are each independently of the other $C_1$–$C_{12}$alkyl.

11. The process of claim 1, wherein $R_4$ and $R_3$ are identical.

12. The process of claim 1, wherein $R_1$ and $R_2$ are identical.

13. The process of claim 12, wherein $R_1$ and $R_2$ are tert-butyl.

* * * * *